US007155042B1

(12) United States Patent  (10) Patent No.: US 7,155,042 B1
Cowan et al.  (45) Date of Patent: Dec. 26, 2006

(54) METHOD AND SYSTEM OF MEASURING CHARACTERISTICS OF AN ORGAN

(75) Inventors: Brett Cowan, Auckland (NZ); Alistair Young, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 09/786,510

(22) PCT Filed: Apr. 26, 2000

(86) PCT No.: PCT/NZ00/00063

§ 371 (c)(1),
(2), (4) Date: Mar. 6, 2001

(87) PCT Pub. No.: WO01/01859

PCT Pub. Date: Jan. 11, 2001

(30) Foreign Application Priority Data

Apr. 21, 1999 (NZ) ...................................... 335321

(51) Int. Cl.
*G06K 9/00* (2006.01)
(52) U.S. Cl. ...................................... 382/128; 382/154
(58) Field of Classification Search ................ 382/128, 382/129, 130–132, 285, 154; 600/443
See application file for complete search history.

(56) References Cited

U.S. PATENT DOCUMENTS

| 4,875,165 A | | 10/1989 | Fencil et al. | |
| 5,273,040 A | | 12/1993 | Apicella et al. | |
| 5,435,310 A | * | 7/1995 | Sheehan et al. | 600/416 |
| 5,608,849 A | | 3/1997 | King, Jr. | |
| 5,687,737 A | * | 11/1997 | Branham et al. | 600/523 |
| 5,800,353 A | | 9/1998 | McLaurin, Jr. | |
| 6,038,466 A | | 3/2000 | Haselhoff | |
| 6,106,466 A | * | 8/2000 | Sheehan et al. | 600/443 |

FOREIGN PATENT DOCUMENTS

| DE | 197 11 401 A1 | 10/1998 |
| WO | 99/18450 | 4/1999 |

OTHER PUBLICATIONS

McInerney et al, "A Dynamic Finite Element Surface Model for Segmentation and Tracking . . . ," Computerized Medical Imaging and Graphics, vol. 19, No. 1, pp. 69-83 (1995).
Abstract of DE 19711401-A1, "Method of spatial representing sectional images, especially . . . ".
Abstract of TW 319687-A, "Compurterised boundary estimation technique e.g., for ultrasonic medical images . . . ".

\* cited by examiner

*Primary Examiner*—Jingge Wu
*Assistant Examiner*—Tom Y. Lu
(74) *Attorney, Agent, or Firm*—Nixon & Vanderhye

(57) ABSTRACT

The invention provides a method of measuring characteristics of an organ or part thereof from multiple images of the organ or part thereof, the method comprising the steps of defining the spatial position of at least two of the images; defining a reference model of the organ or part thereof scaled according to the distance between reference markers on the images; defining one or more boundary guide points associated with one or more images for which the spatial positions have been defined; converting the guide points to three-dimensional coordinates; defining an estimate model by fitting the reference model to the guide points; and calculating the characteristics from the estimate model. The invention also provides a system and a computer program for measuring characteristics of an organ or part thereof of a subject from multiple images of the subject's organ or part thereof.

30 Claims, 15 Drawing Sheets

METHOD AND SYSTEM OF MEASURING CHARACTERISTICS OF AN ORGAN

FIELD OF THE INVENTION

The invention relates to a method and system of measuring characteristics of an organ or part thereof. The method and system of the invention are particularly suited to measuring cardiac function, volume, and/or mass of a ventricle of the heart of a subject from multiple image slices obtained by magnetic resonance imaging (MRI). The method and system of the invention may also be used to calculate the volume and/or mass and other characteristics of other organs such as a lung, kidney or brain, to measure the position of the wall of a blood vessel for the purposes of analysis of flow, or to calculate the volume and/or mass of a bone, tumour or cyst.

BACKGROUND TO INVENTION

Ventricular mass, volumes and wall thickness at end diastole and end systole are essential clinical parameters for diagnosis and management of many cardiac diseases. Magnetic resonance imaging (MRI) may be used to estimate heart wall motion by reconstructing the shape and motion of the left ventricle.

MRI is also able to provide accurate and precise estimations of ventricular mass, volume and wall thickness, since it is a true 3-dimensional method which is not dependent on geometric assumptions and is not limited in the position or orientation of the possible images, unlike other methods, such as for example echocardiography or computed tomography.

Recent advances in MRI allow the acquisition of 10 to 20 MRI images or slices in short and long axis or arbitrary orientations, each with 10 to 25 frames through the cardiac cycle in real time, or ten to fifteen minutes or less, which is a clinically acceptable time. Previous studies have shown that the summation of areas outlined in short axis MRI slices gives more accurate and reproducible estimates of volume than echocardiography or LV angiography.

A major limitation of the MRI slice summation method is the prohibitive time required to outline the endocardial and epicardial boundaries of the left ventricle in each slice. This severely limits application of the use of the technique to routine clinical care.

In the past, many semi-automated image segmentation algorithms have been applied to this problem, but these solutions are frequently not sufficiently robust and accurate for routine clinical use. In particular the image pixel intensities are insufficient to adequately constrain the segmentation problem, due to the limited temporal and spatial resolution, presence of image artifacts, and lack of contrast between blood and muscle. The amount of time spent on manual editing and correction of contours obtained from these previous solutions renders automated methods nearly as slow as manual contouring in clinical practice.

Other techniques apply model fitting techniques to estimate characteristics of organs such as the left ventricle. T McInerney and D Terzopoulos in "A Dynamic Finite Element Surface Model for Segmentation and Tracking in Multidimensional Medical Images with Application to Cardiac 4D Image Analysis", Computerized Medical Imaging and Graphics 19:69–83; 1995 describe a deformable "balloon" model that is topologically isomorphic to a sphere for use in estimating volume and motion of the left ventricle. PCT international patent publication WO 99/18450 to Philips AB titled "Method of and Device for Imaging an Object by means of Magnetic Resonance" describes the use of an ellipsoid to model the left ventricle. Both techniques require the use of edge detection algorithms and in doing so suffer from the disadvantages discussed above.

SUMMARY OF INVENTION

In broad terms in one aspect the invention comprises a method of measuring characteristics of an organ or part thereof of a subject from multiple images of the subject's organ or part thereof, the method comprising the steps of defining the spatial position of at least two of the slices; defining a reference model of the organ or part thereof scaled according to the distance between the slices; defining one or more boundary guide points associated with one or more slices for which the spatial positions have been defined; converting the guide points to three-dimensional coordinates; defining an estimate model by fitting the reference model to the guide points; and calculating the characteristics from the estimate model.

In broad terms in another aspect, the invention comprises a system for measuring characteristics of an organ or part thereof of a subject from multiple image slices of the subject's organ or part thereof, the system comprising a memory in which is stored the spatial position of at least two of the slices; reference model definition means arranged to define a reference model of the organ or part thereof scaled according to the distance between the slices; boundary guide point definition means arranged to define one or more boundary guide points associated with one or more slices for which the spatial positions are stored in the memory; conversion means arranged to convert the guide points to three-dimensional coordinates; estimate model definition means arranged to define an estimate model by fitting the reference model to the guide points; and calculation means arranged to calculate the characteristics from the estimate model.

In yet another form the invention comprises a computer program for measuring characteristics of an organ or part thereof of a subject from multiple image slices of the subject's organ or part thereof, the program comprising storage means arranged to store the spatial position of at least two of the slices; reference model definition means arranged to define a reference model of the organ or part thereof scaled according to the distance between the slices; boundary guide point definition means arranged to define one or more boundary guide points associated with one or more slices for which the spatial positions are stored in the memory; conversion means arranged to convert the guide points to three-dimensional coordinates; estimate model definition means arranged to define an estimate model by fitting the reference model to the guide points; and calculation means arranged to calculate the characteristics from the estimate model.

BRIEF DESCRIPTION OF THE FIGURES

Preferred forms of the invention will now be described, by way of example, with reference to the accompanying figures in which.

DETAILED DESCRIPTION OF PREFERRED FORMS

Figure 1:
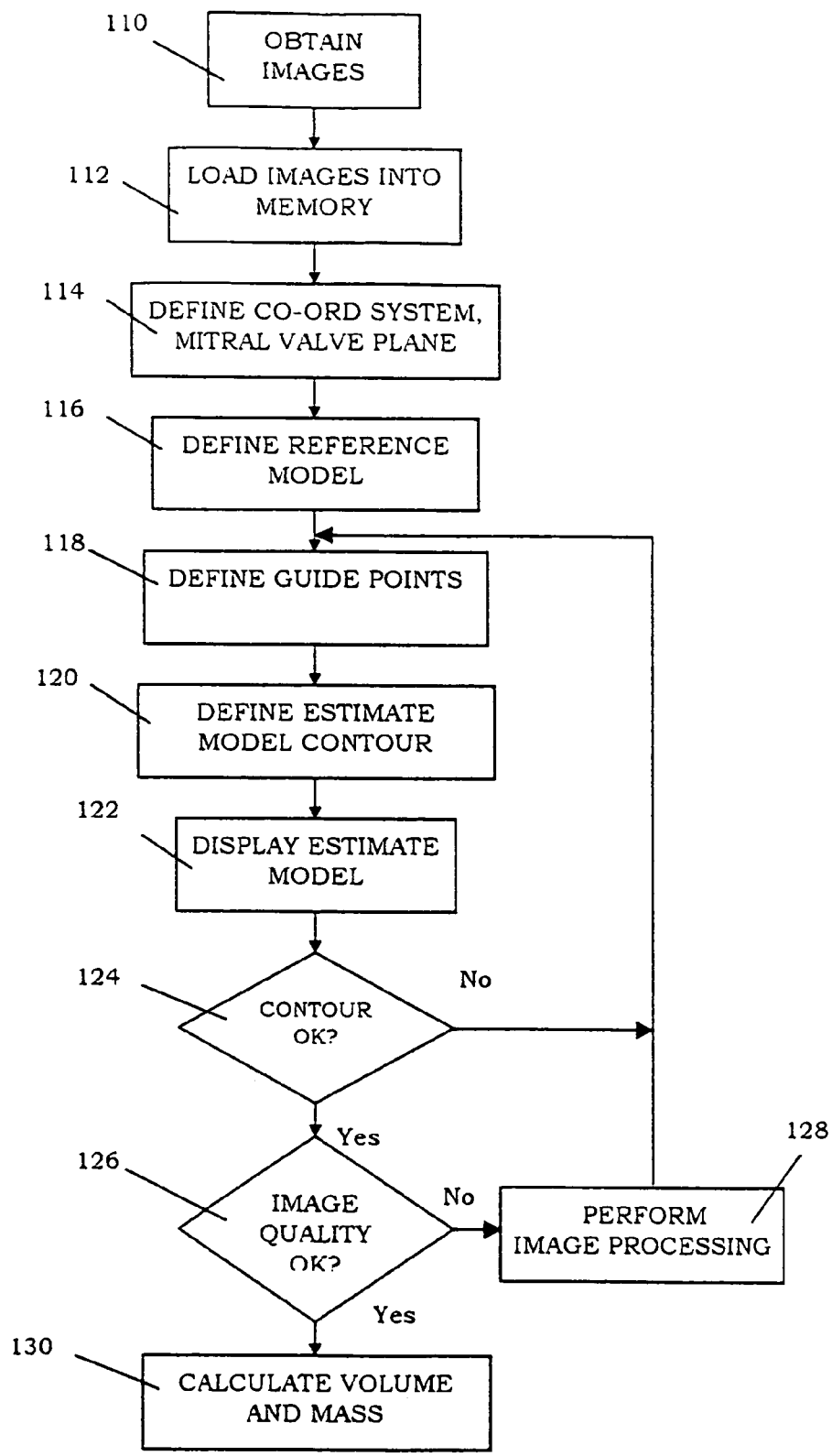
FIG. 1 is a flow chart outlining a preferred form of the method of the invention.

FIG. 1 sets out a preferred form of method of the invention.

A number of images are first obtained of the left ventricle of a subject as indicated at. The images could be acquired from an MRI scanner, or may alternatively be acquired by an ultra-fast CT, 3-dimensional ultrasound machine or echocardiography, or other suitable imaging modality. The images could also be obtained from confocal microscopy, electron microscopy or histology. The images are typically 2-dimensional cines or movies of the heart and are taken at standard orientations, for example, short axis and long axis, or at entirely arbitrary positions depending on the nature of the pathology and imaging modality.

The preferred images are acquired in a number of spatial locations, having a lowest or apical slice, a highest or basal slice, one or more middle slices and one or more long axis slices. The preferred images are acquired in between 2 and preferably 20 spatial locations, and typically 12 spatial locations. Preferably images in each of these spatial locations are obtained at multiple frames through the cardiac cycle. The preferred number of frames is 10 to 25.

Conventional MRI imaging apparatus produces images having image headers. The image header in each image generally comprises an extensive data list including patient name and scan parameters at the beginning of each image. The image header also provides data representing the spatial position and temporal position of each slice or frame.

The images are loaded into memory as indicated at 112. The preferred memory forms part of a computer having a CPU, input devices and a display device such as a VDU. The preferred input devices comprise a keyboard, mouse and disk drive, typically a networked magneto-optical disc drive and/or CD ROM drive. Images may also be transferred over a network. The preferred memory comprises a hard disk drive suitable for storing the images.

The preferred computer comprises a SUN SparcStation, SGI work station, PC, or similar having at least 128 MB Ram or similar. The computer has loaded on it suitable operating system software, such as SOLARIS, IRIX, WINDOWS or LINUX. The preferred computer is arranged to execute application software in which the present invention has been developed. The preferred application software is written in C++, using OpenGL, OpenInventor and Xwindows for graphical interfaces.

Figure 2:
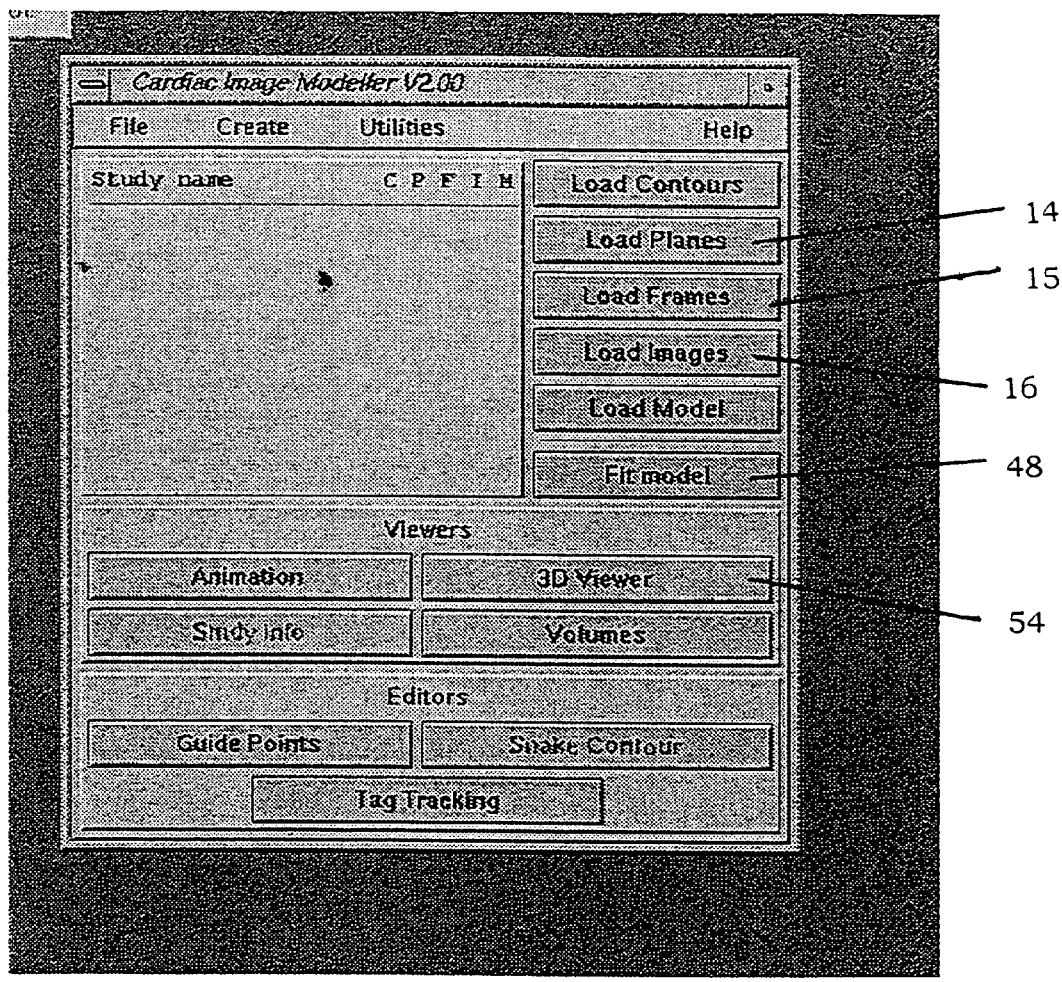
FIG. 2 shows the main window of a preferred form of an application program in which the invention is implemented.

Referring to FIG. 2, the user is presented with a main window from which a number of options may be selected. The option to load planes is indicated at 14 which loads the three-dimensional position of the images and the option to load frames is indicated at 15 which loads the position of the images in time. This spatial and temporal information is generally included in the image headers. The option to load images is indicated at 16. Each separate image location is displayed in a second window at the first phase of imaging simultaneously.

Various parameters may be specified by the user at the time of loading the images, for example Model Type, Fit Type and Data Set. The user may also specify directory names for directories such as a Data Directory, a Model Directory and a Script Directory.

As shown at 114 in FIG. 1, the next step is to define a three-dimensional coordinate system from two or more of the slices for which the spatial positions have been defined. The main window of FIG. 2 presents to the user an option to enter the guide points editor. The guide points editor loads the editor window shown in FIG. 3. The editor window includes panel 20 which in the preferred form displays thumbnail images of the images stored in the memory. Panel 22 displays an enlarged image of one of the images displayed in panel 20. The preferred form window shown in FIG. 3 also provides the user with the ability to zoom and pan images and to adjust brightness and contrast. The user may select the image to be displayed in panel 22 by, for example, clicking on one of the thumbnails displayed in panel 20.

Figure 3:
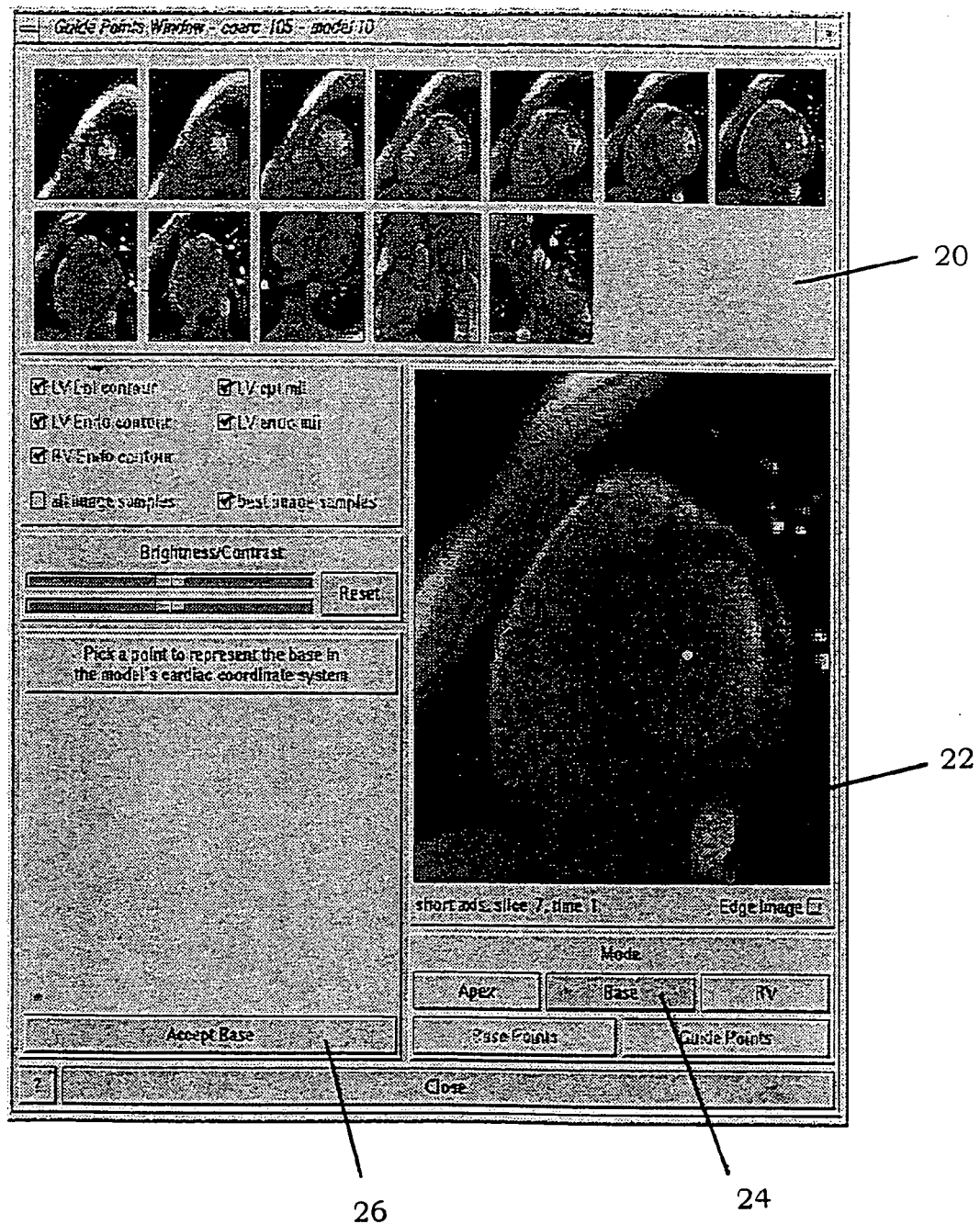
FIG. 3 shows a guide points window and the preferred method of selecting the left ventricular basal slice from this window.

The user first selects the basal or highest short axis slice in panel 20, clicking on the thumbnail image to display the enlarged image in panel 22. In FIG. 3 the user has selected the basal slice which is described below panel 22 as the seventh short axis image obtained during the first time interval or frame.

The user selects the Base option indicated at 24. A prompt is displayed for the user to pick a point to represent the base in the model's cardiac coordinate system. The user selects a point in the centre of the ventricular image by clicking in panel 22. Once the desired base has been selected the user selects the option to accept the base indicated at 26.

Figure 4:
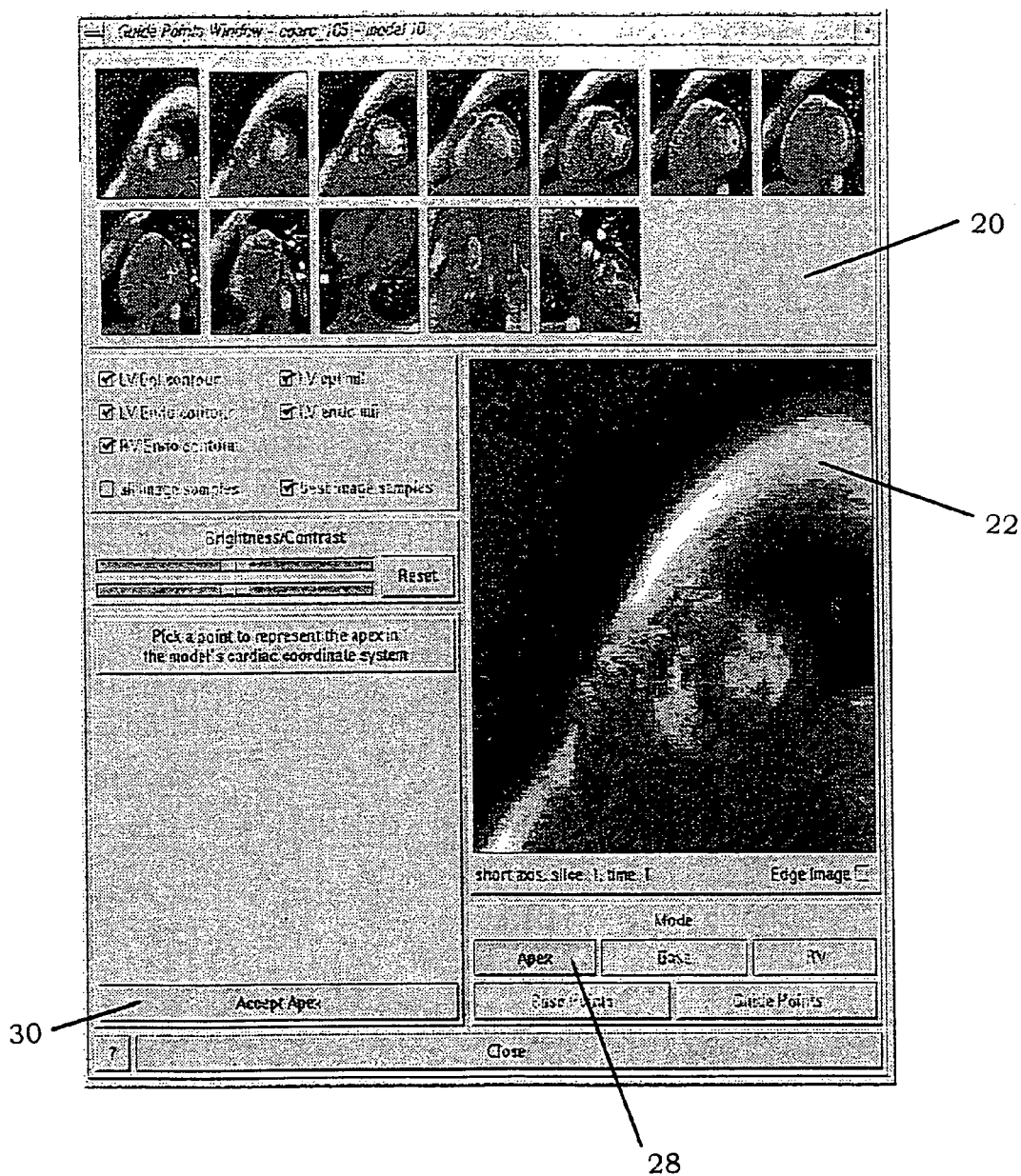
FIG. 4 shows the preferred method of selecting the left ventricular apical slice from the window of FIG. 3.

Referring to FIG. 4, the user repeats the procedure to select the apex of the object. The user selects the Apex option indicated at 28. A prompt is displayed for the user to pick a point representing the apex and the user then selects the point in panel 22. Once the desired apex has been selected the user accepts the apex as indicated at 30.

If the spatial position of the basal slice and the apical slice is known then land marks may be determined, for example the long axis. The software calculates the length and position of the long axis by defining a line in 3-dimensional space between the two points selected by the user.

Figure 5:
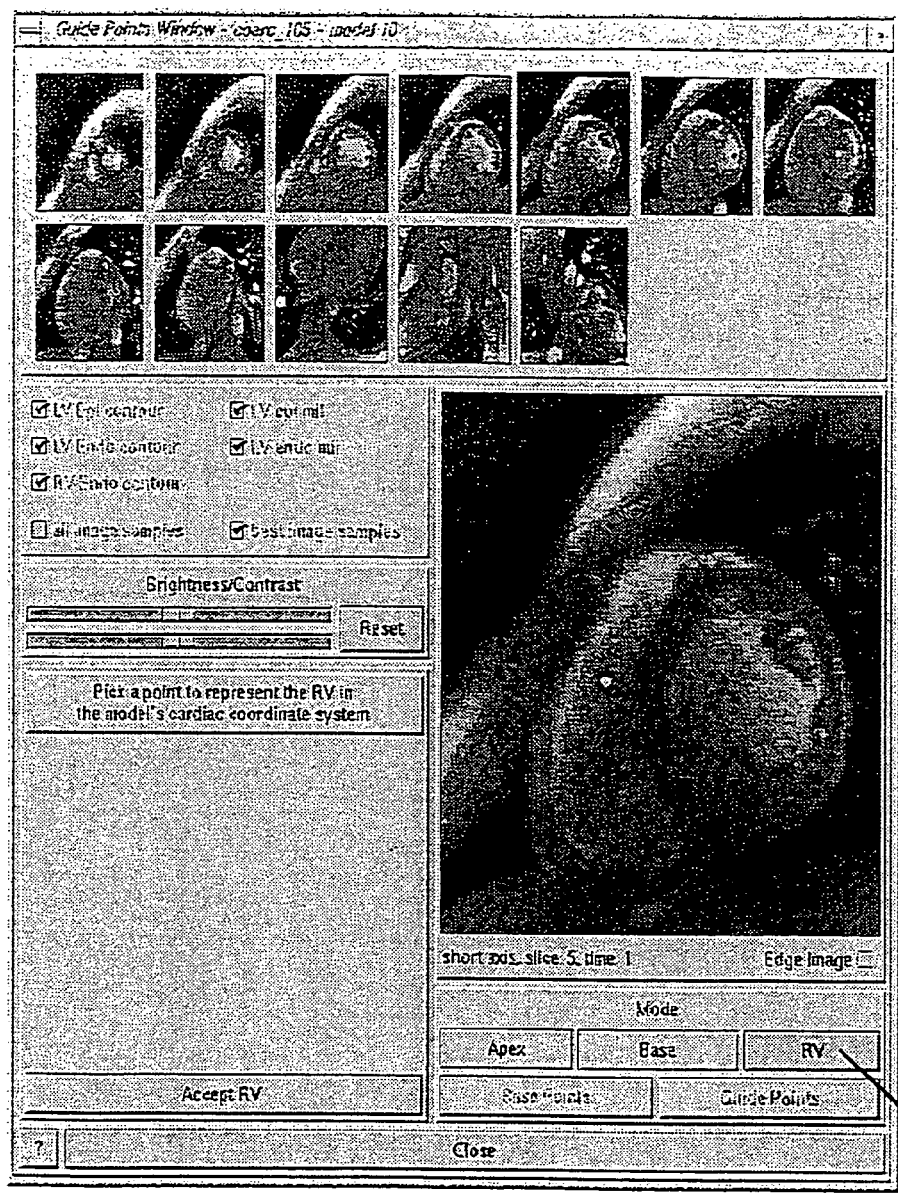
FIG. 5 shows the preferred method of entering characteristics of the right ventricle from the window of FIG. 3.

As shown in FIG. 5, the user is not limited to defining the co-ordinate system on the left ventricle. By selecting the option indicated at 35 the user may select different points or landmarks to analyse, for example, the right ventricle.

Figure 6:
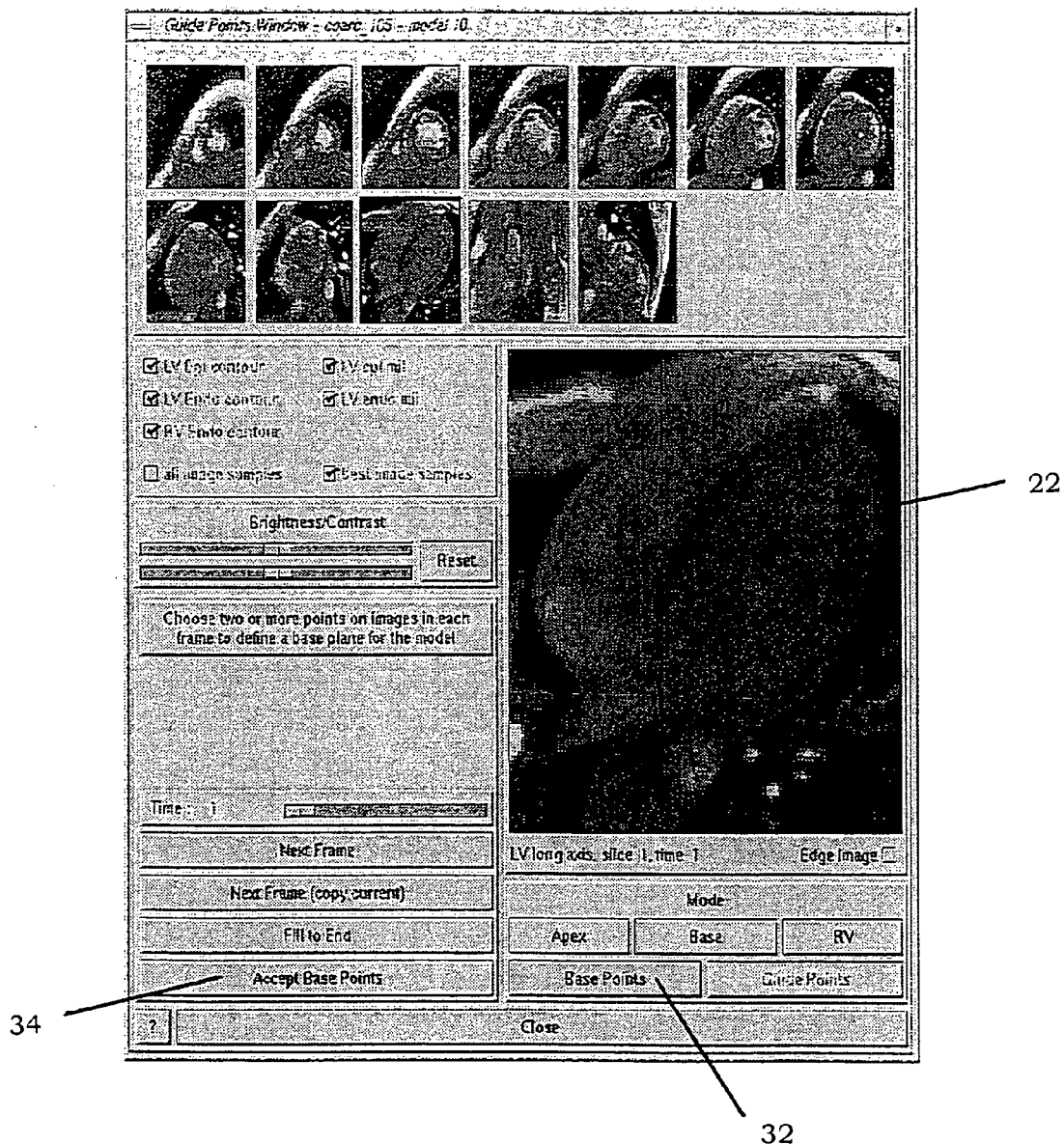
FIG. 6 shows the preferred method of defining the base or mitral valve plane from the window of FIG. 3.

As shown in FIG. 6, the user may display in panel 22 an image taken of the long axis of the object, as indicated by the description below panel 22. The user selects the Base Points option 32 which then prompts the user to choose two or more points on the image to define the maximum extent for estimate model and calculate volumes of, for example, the mitral valve plane. The user selects the points by clicking in panel 22 and once the desired points have been selected the user accepts the base points indicated at 34. Further options may also be provided, for example advancing the image displayed in panel 22 to the next frame.

It will be appreciated that the user does not need to define the axis by selecting the centre of the ventricle in the basal and apical slices. The user may instead define the centre of the left ventricle in two slices which are not the basal or apical slices. The software may then calculate the position of the long axis by defining a line in 3-dimensional space between these two points. The length of the long axis of the left ventricle may then be calculated separately from the distance between the basal and apical slices if the spatial position of the slices is known.

As shown at step 116 in FIG. 1, the software defines a reference model of a left ventricle. The preferred reference shape closely approximates the generic shape of a left ventricle. The reference model may be constructed from real patient data, but does not have to be absolutely accurate in terms of an individual patient. The reference model may be defined as an analytical function, as a coordinate system, or as data points.

The preferred reference model is a finite element model consisting of at least 16 elements, typically 16 to 40, each with cubic interpolation in the circumferential and longitudinal directions. Linear interpolation is used to couple the endocardial and epicardial surfaces into a coherent 3-D model. The preferred model is defined in a polar coordinate system in which the radial coordinate of the model is fitted as a function of the two angular coordinates in the circumferential and longitudinal directions respectively. The preferred initial shape of the reference model is a regular ellipsoid, typically a prolate spheroid, obtained by setting the endocardial and epicardial surfaces to a constant radial value. The preferred reference model is scaled according to the length of the long axis of the left ventricle of the subject with the extent of the model in the longitudinal direction set to correspond to the point identified on the most basal slice of the left ventricle in the long axis.

The preferred estimate model is obtained by a least squares finite element modelling process in which the left ventricle is divided into a number of rectangular segments or elements. Each element defines a bicubic spline surface for part of the endocardial and epicardial surfaces of the left ventricle. It is important to ensure continuity in the surface defined by adjacent elements. To ensure continuity, adjacent elements are constrained to have the same position and slope on each side of the join. Ensuring continuity in this way eliminates or at least reduces ridges and sharp transitions between adjacent elements.

Within each element, the geometric coordinate field x is given as a function of element or material coordinates $\xi$ by a weighted average of nodal values:

$$x(\xi_1, \xi_2, \xi_3) = \sum_n \Psi_n(\xi_1, \xi_2, \xi_3) \lambda^n \quad (1)$$

where $\lambda^n$ are the nodal values, $\Psi_n$ are the element basis functions which give the relative weighting of each nodal value, and ($\xi_1$, $\xi_2$, $\xi_3$) are the element co-ordinates.

The geometric field $\lambda$ is defined to be the radial co-ordinates in the polate spheroidal coordinate system:

$$x = f \cos h(\lambda)\cos(\mu) y = f \sin h(\lambda)\sin(\mu)\cos(\theta) z = f \sin h(\lambda)\sin(\mu)\sin(\theta) \quad (2)$$

where ($\lambda$, $\mu$, $\theta$) are the radial, longitudinal and circumferential co-ordinates of the polar system and (x, y, z) are the corresponding rectangular Cartesian co-ordinates. The focal length f of the polate system is preferably chosen so that the $\lambda=1$ surface gives a good initial approximation of the left ventricular epicardial surface, providing an overall scale factor for the ventricle.

Previously defined points are used to determine the initial position of the model with respect to the images. These are:

a) the location of the central axis at the center of the LV in an apical short axis image
b) the location of the central axis at the center of the LV in a basal short axis image
c) the approximate centroid of the right ventricle
d) a set of points describing the mitral valve plane.

A model-based coordinate system is then constructed with the origin placed on the central axis of the LV one third of the distance from the base to the apex. Nodes are placed at equally spaced intervals in the two angular coordinates ($\mu$, $\theta$) and at a constant radial coordinate ($\lambda$). The centroid of the RV has $\theta=0$ and the extent of the model in the $\mu$ direction is governed by the basal margin points. The distance from apex to base is used to determine the focal length of the prolate system and provides an overall scale factor for the LV.

Each guide point is projected onto the model along lines of constant $\mu$ and $\theta$ and only the $\lambda$ field is fitted by linear least squares.

Figure 7:
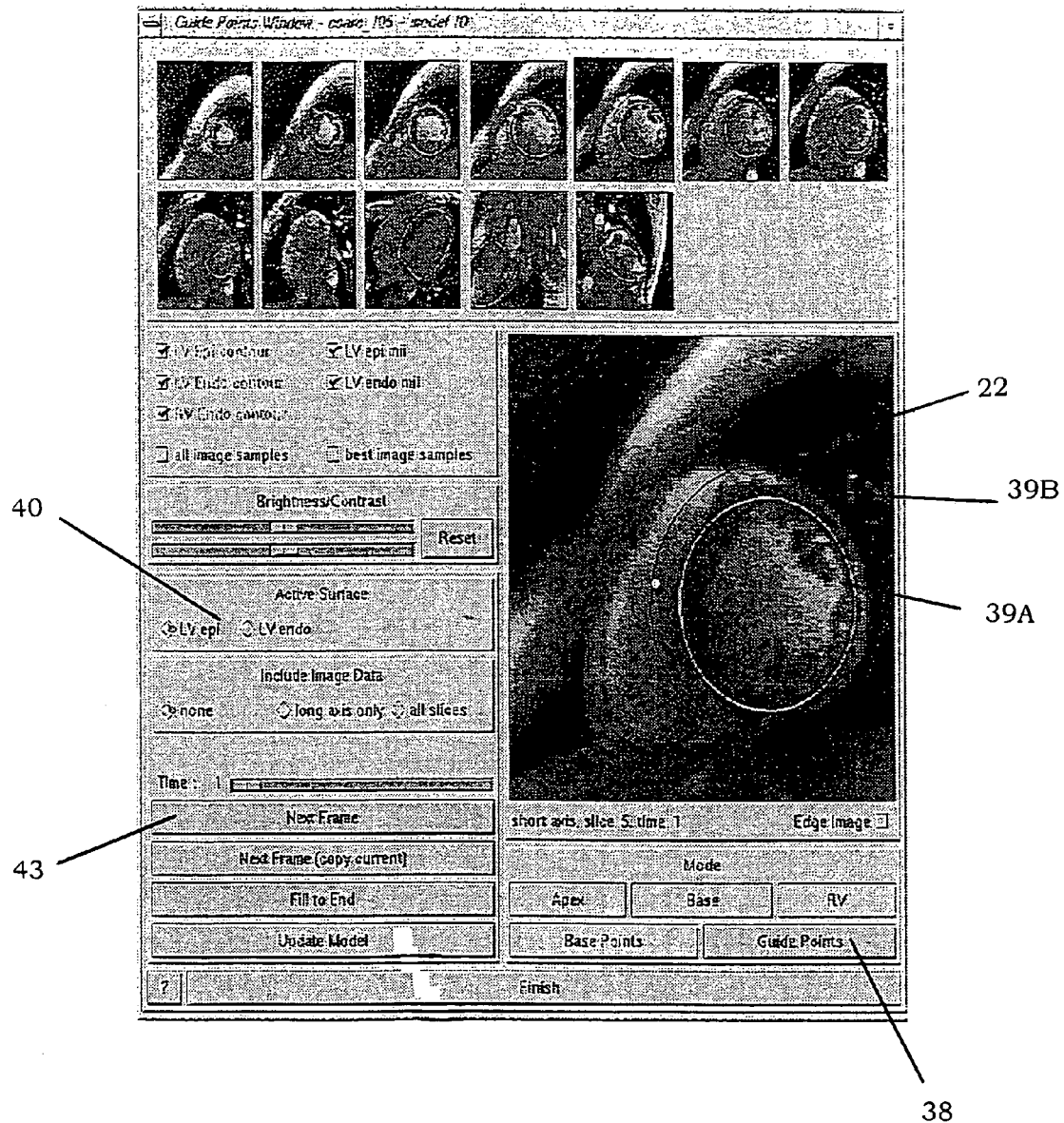
FIGS. 7 to 10 illustrate a method of selecting boundary guide points from the window of FIG. 3.

As shown at 118 in FIG. 1, the next step is to define one or more guide points on one or more slices for which the spatial positions have been defined. Referring to FIG. 7 the user is presented with the option indicated at 38 of defining guide points. The user then selects and displays in panel 22 any one of the slices stored in the memory. The image of the subject organ is displayed in panel 22. A representation of the reference model is preferably superimposed on the image of the subject organ. In the preferred form, a representation of the intersection of the reference model with the image slice superimposed on the image slice, as indicated by contour lines 39A and 39B.

Figure 8:
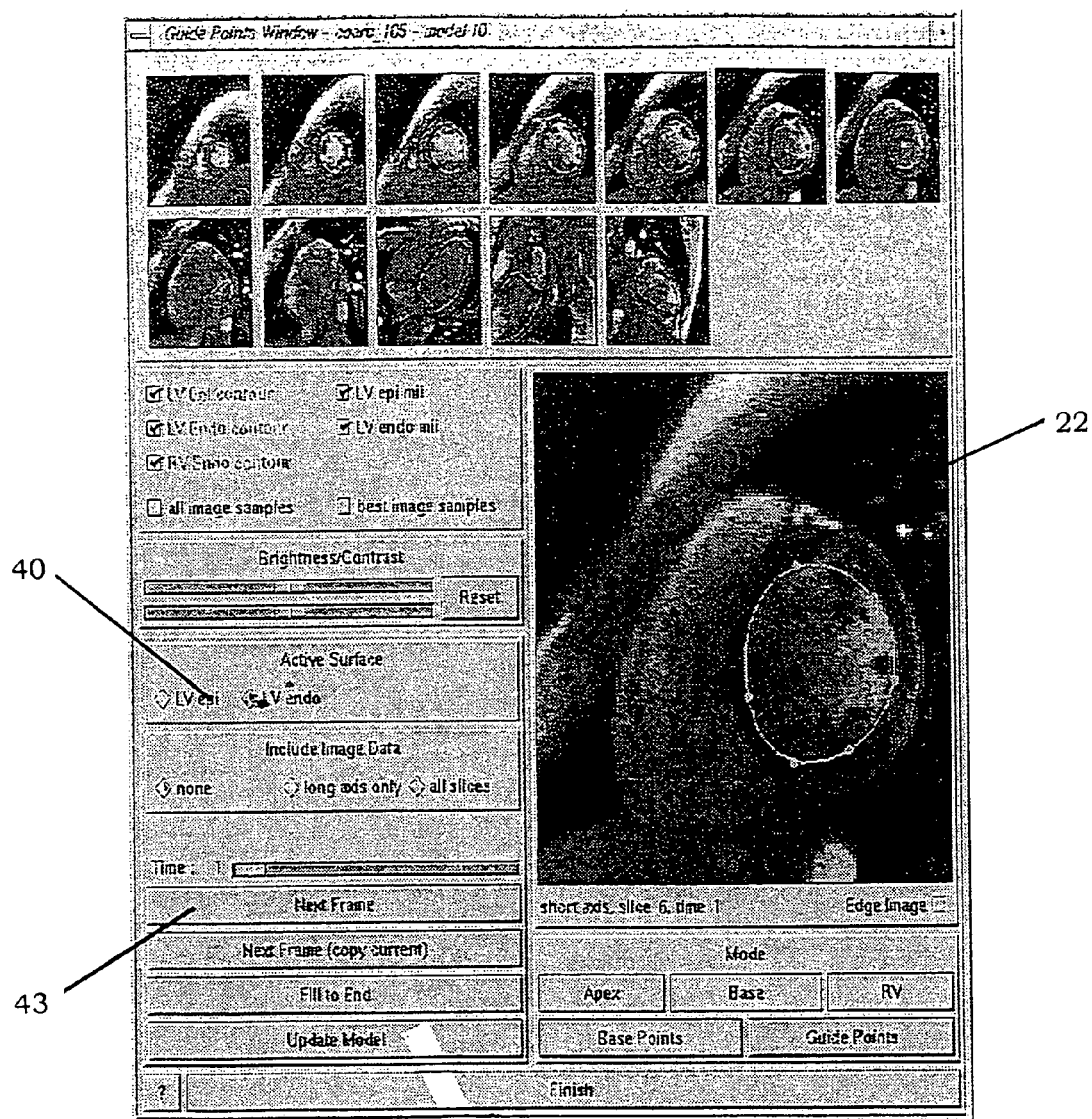

The user first selects the active surface which is being defined as indicated at 40. In FIG. 8 the user has selected the left ventricular endocardial boundary as the active surface. Using a mouse, the user defines one or more boundary guide points on the selected slice by clicking in panel 22. These guide points, in combination with the reference model, define the endocardial or epicardial boundaries of the heart. Preferably three to four endocardial boundary guide points and three to four epicardial boundary guide points are entered for each slice, although the user is able to enter a large number of boundary guide points for a particular slice or may instead ignore a slice and enter no boundary guide points for it.

As the user defines the guide points, the system converts these guide points to three-dimensional coordinates from the image position in space for each boundary guide point, and fits the model by forcing the model to adhere closely to the guide points, as will be discussed below.

Where a number of image frames are stored in memory, the user may advance to the next frame by clicking on the Next Frame option indicated at 43.

Figure 9:
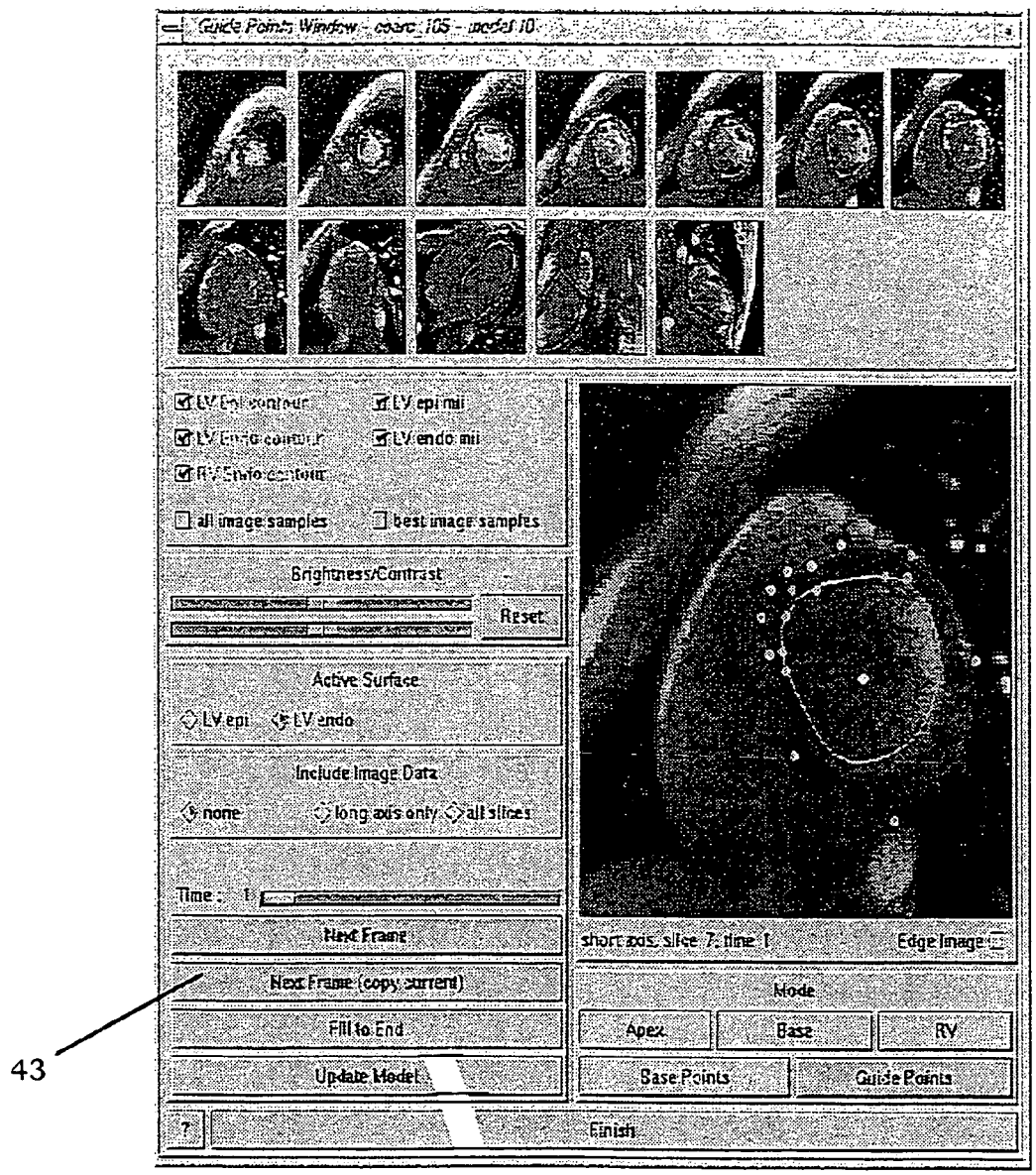
Figure 10:
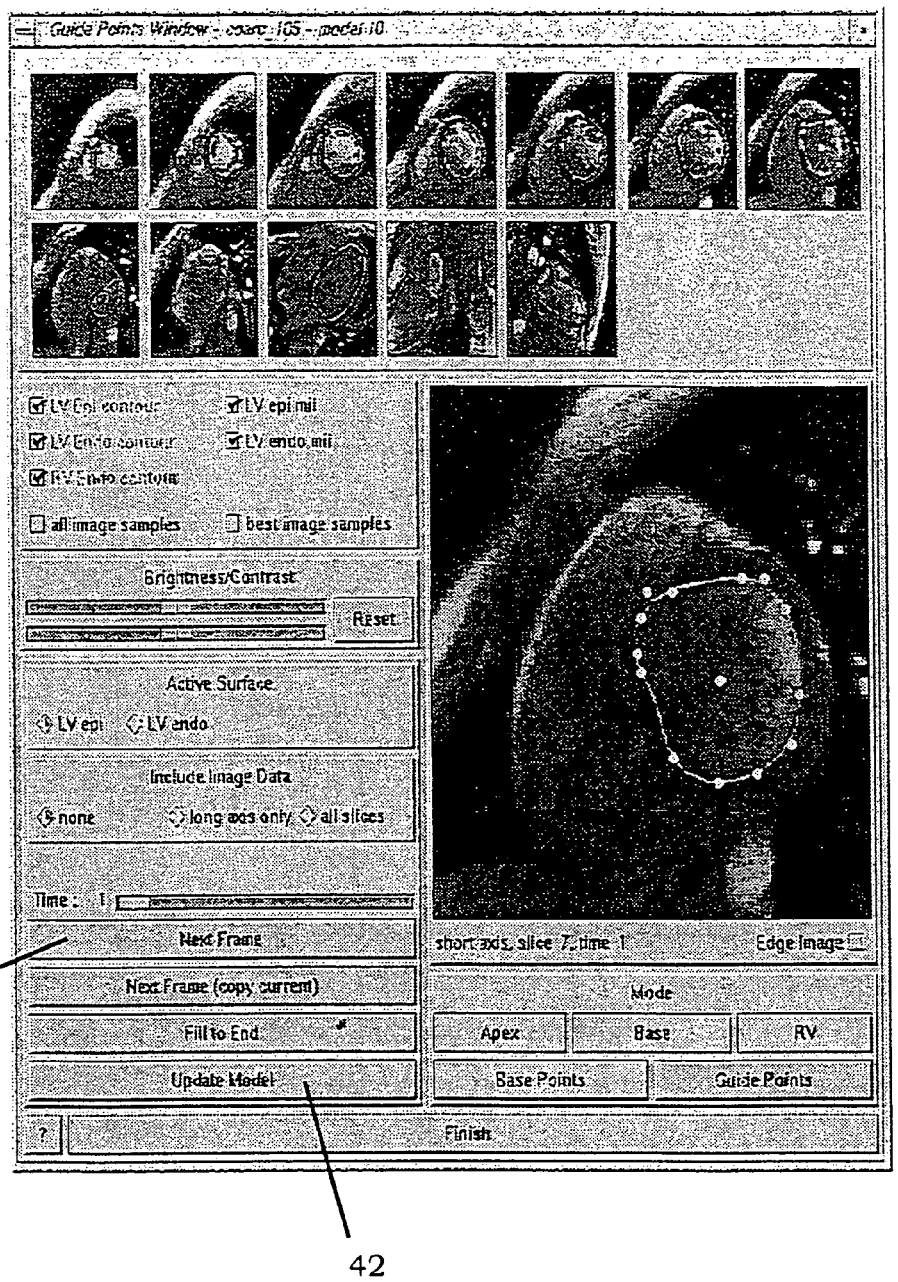

FIGS. 9 and 10 further illustrate the process by which the boundary points are defined by the user. The user is defining the endocardial boundary of an image slice different to the one shown in FIG. 7. In FIGS. 9 and 10 the user is defining the epicardial and endocardial boundaries respectively for a further image.

It will be appreciated that where an organ other than the left ventricle is to be modelled, the reference model will be varied. For example, where the invention is used to model the right ventricle, lung and/or kidney, a different reference model will be defined.

The next step indicated at 120 in FIG. 1 is to form an estimate model by fitting the reference model to the guide points. This process could be initiated automatically whenever the user selects the Next Frame option indicated at 43 in FIGS. 7 to 10, or may be updated automatically in real time with the insertion or deletion of a guide point or any change in guide point position.

The preferred method for incorporating the reference model data is to minimise an error function consisting of the sum of a smoothing term and a term penalising the distance between each boundary guide point and the corresponding reference model position.

The preferred smoothing term penalises changes in slope and curvature around the left ventricle, allowing the reference model to realistically interpolate guide point data where the data is sparse.

The preferred penalty is introduced into the least squares method which penalises only the sum of the squared deviations from the boundary guide points to the reference model surface. In particular, the first and second derivatives of the surfaces are constrained to be minimised within the least squares fit to prevent rippling and other abnormalities. In this sense, the smoothing can be viewed as weighting the estimate model more toward the reference model than the boundary guide points so that the reference model is imposed more strongly where there are no or insufficient boundary guide points.

One preferred smoothing method is set out more particularly below, in which the error function minimised is:

$$E = S(\lambda) + \sum_g (\lambda(\xi_g) - \lambda_g)^2 \qquad (3)$$

where $\lambda_g$ are the positions of the guide point data and $\lambda(\xi_g)$ are the model positions at element co-ordinates $\xi_g$ corresponding to $\lambda_g$. The element co-ordinates are preferably found by projecting the guide data onto the model along lines of constant $\mu$ and $\theta$. $S(\lambda)$ denotes a smoothing term included in the error function to constrain the model to smoothly interpolate between the sparse guide points.

$S(\lambda)$ is preferably a weighted Sobolev norm which penalizes the displacement of the estimate model from the reference model.

$$S(\lambda) = \int_\Omega \alpha_1 \left[\frac{\partial u}{\partial \xi_1}\right]^2 + \alpha_2 \left[\frac{\partial u}{\partial \xi_2}\right]^2 + \beta_1 \left[\frac{\partial^2 u}{\partial \xi_1^2}\right]^2 + \beta_2 \left[\frac{\partial^2 u}{\partial \xi_2^2}\right]^2 + \qquad (4)$$
$$\gamma_1 \left[\frac{\partial^2 u}{\partial \xi_1 \partial \xi_2}\right]^2 + \gamma_2 \left[\frac{\partial^2 u}{\partial \xi_1 \partial \xi_3}\right]^2 + \gamma_3 \left[\frac{\partial^2 u}{\partial \xi_2 \partial \xi_3}\right]^2 d\Omega$$

where $u=\lambda-\lambda^*$ where $\lambda^*$ is the reference model. The weights $\alpha_1$ and $\alpha_2$ penalize the slope of the displacement field in the circumferential and longitudinal directions respectively, the weights $\beta_1$ and $\beta_2$ penalize curvature and the weights $\gamma_1$, $\gamma_2$ and $\gamma_3$ couple slopes between directions. Typical smoothing weights are $\alpha_1=\alpha_2=0$, $\beta_1=\beta_2=0.001$, $\gamma_1=\gamma_2=\gamma_3=0.01$.

The resulting estimate model incorporates endocardial and epicardial boundary guide points, the long axis of the left ventricle, reference model data and smoothing constraints to produce endocardial and epicardial left ventricular surfaces in three or four dimensions closely approximating the true surfaces represented in the images.

Having defined these surfaces, the software may then calculate the intersection of the image slices with the surfaces and display the estimate model as indicated at 122 in FIG. 1. The intersections are each represented by two lines, one line representing the endocardium and the other line representing the epicardium which are close to the edges on the images.

Having calculated endocardial and epicardial surface boundaries on each image, image(s) are then evaluated, preferably by the user, for acceptable contours as indicated at 124 and acceptable image quality as indicated at 126. The software may then perform local image processing as indicated at 128 to further improve the quality of the left ventricle boundary edges displayed in the images. The use of local image processing is not essential to the invention. Where provided, it may be invoked by the user. An edge is characterized by an abrupt change in intensity indicating a boundary, and is called a discontinuity. In general an edge is often seen as a slow change in grey level values between connected pixels. While a boundary edge may be readily apparent to the human eye, it can be difficult for software to detect.

Prior art methods of detecting discontinuities or edges include running a mask or window over the image, or by applying a known edge enhancing filter such as a Roberts, Sobel or Laplacian operator. Applying such a filter to an entire image in order to find boundary edges is computationally expensive. Using the present invention, the endocardial and epicardial boundaries have been estimated with the estimate model. The software therefore can calculate the likely position of a boundary edge in an image. An a priori technique may then be applied to guide the search for the boundary in the image.

In one method, radial lines may be drawn extending through both the endocardial and epicardial boundaries. An edge filter may be applied at the intersection of these boundaries and the radial line to determine the points on the radial line most likely to represent the endocardial and epicardial edges.

Further local processing could also include thresholding, for example grey-scale thresholding. All pixel values falling between two threshold values $T_1$ and $T_2$ retain their grey-scale values but all pixel values outside this interval are set to zero. Such multiple thresholds may be applied to reduce the number of grey-level values in an image, thereby enhancing the contrast. Thresholding may be applied, for example, to contrast the area in the image inside the endocardial boundary, from the area between the endocardial and epicardial boundaries, and/or the area outside the epicardial boundary.

Local image processing and thresholding as described above may generate additional data points which may be added to the existing boundary guide points. The estimate model contour may then be redefined based on the additional data points so that the relationship to the actual images is improved.

The additional data points obtained from local image processing and thresholding may be assigned less weight than boundary guide points selected by the user, as it will be appreciated that these additional data points may be less reliable than those selected by the user. The generated data points may be displayed to the user in order to identify where additional guide points are needed to improve the estimate model, for example, where a contour has missed the actual edge.

It will be appreciated that where image processing is performed, it is performed at a local level. It is assumed that the edge is in a particular region. Image processing is computationally expensive and in the past has been performed on an entire image or slice. Using the invention, it is possible to determine the approximate position of the region so that image processing can be concentrated on that region, significantly reducing the processing time. Where the local image processing is unable to determine the location of an edge, the estimate model will be determined primarily from the guide points defined by the user, the reference model, and smoothing parameters.

The software may then define the final estimate model surfaces from the finite element modelling process, with the inclusion of data points obtained by local image processing. The intersection of this surface with the image slices permits the software to display on the original images the left ventricular endocardial and epicardial boundary walls. The step of drawing the estimate model is indicated in FIG. 1 at 122.

The number of guide points can be reduced substantially if the images are of good quality and the image processing is able to accurately define the edges and guide the estimate model on to them.

As shown in FIG. 2, the main window presents to the user the option of viewing the images in three dimensions, indicated at 54. On selecting this option the user is presented with a 3D viewer window as will be more particularly described with reference to FIGS. 11 and 12.

Figure 11:
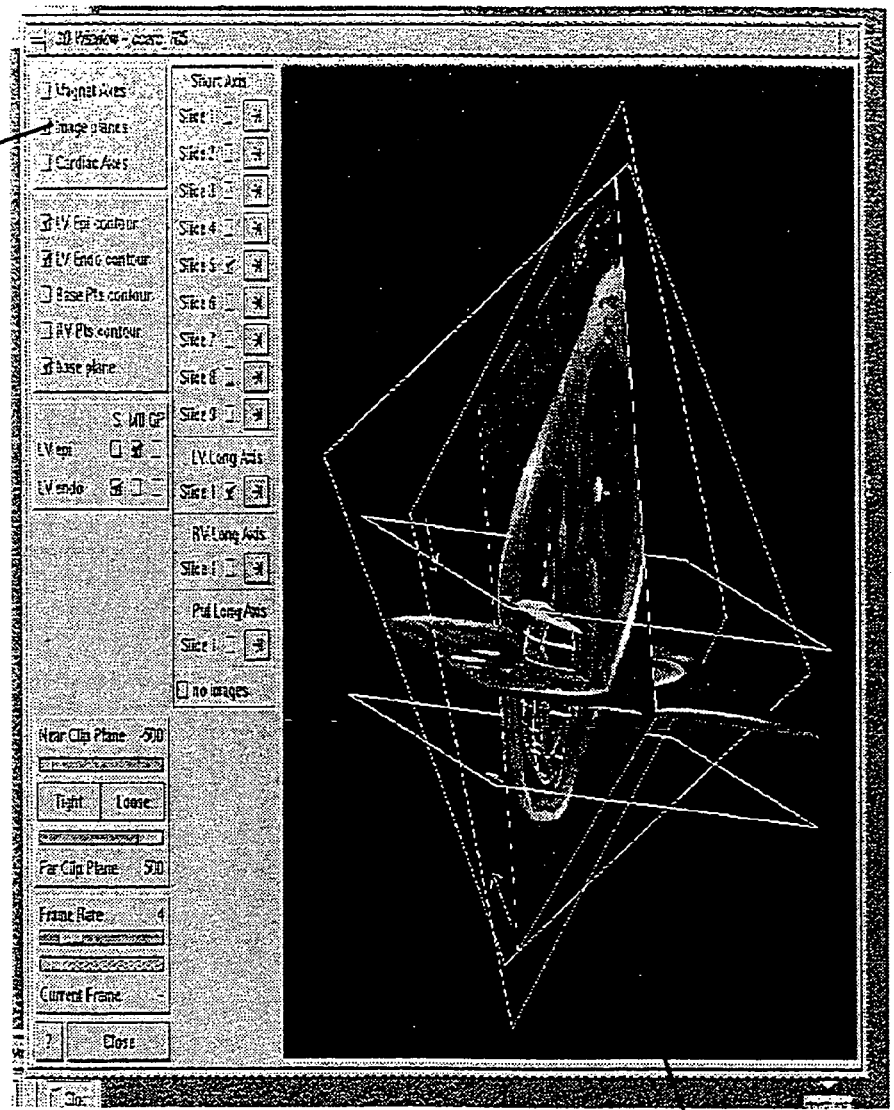
FIGS. 11 and 12 show a preferred window for viewing the model.

Referring to FIG. 11, the window includes panel 56 in which images are displayed. The user has the option of selecting image planes as the desired view as indicated at 124. Where the Image planes option is selected, the user may select which image slices to display in panel 56. In FIG. 11 the user has selected the long axis slice and the fifth short axis slice to display in panel 56. Also displayed in panel 56 are the intersections of the estimate model with the original image planes.

Figure 12:
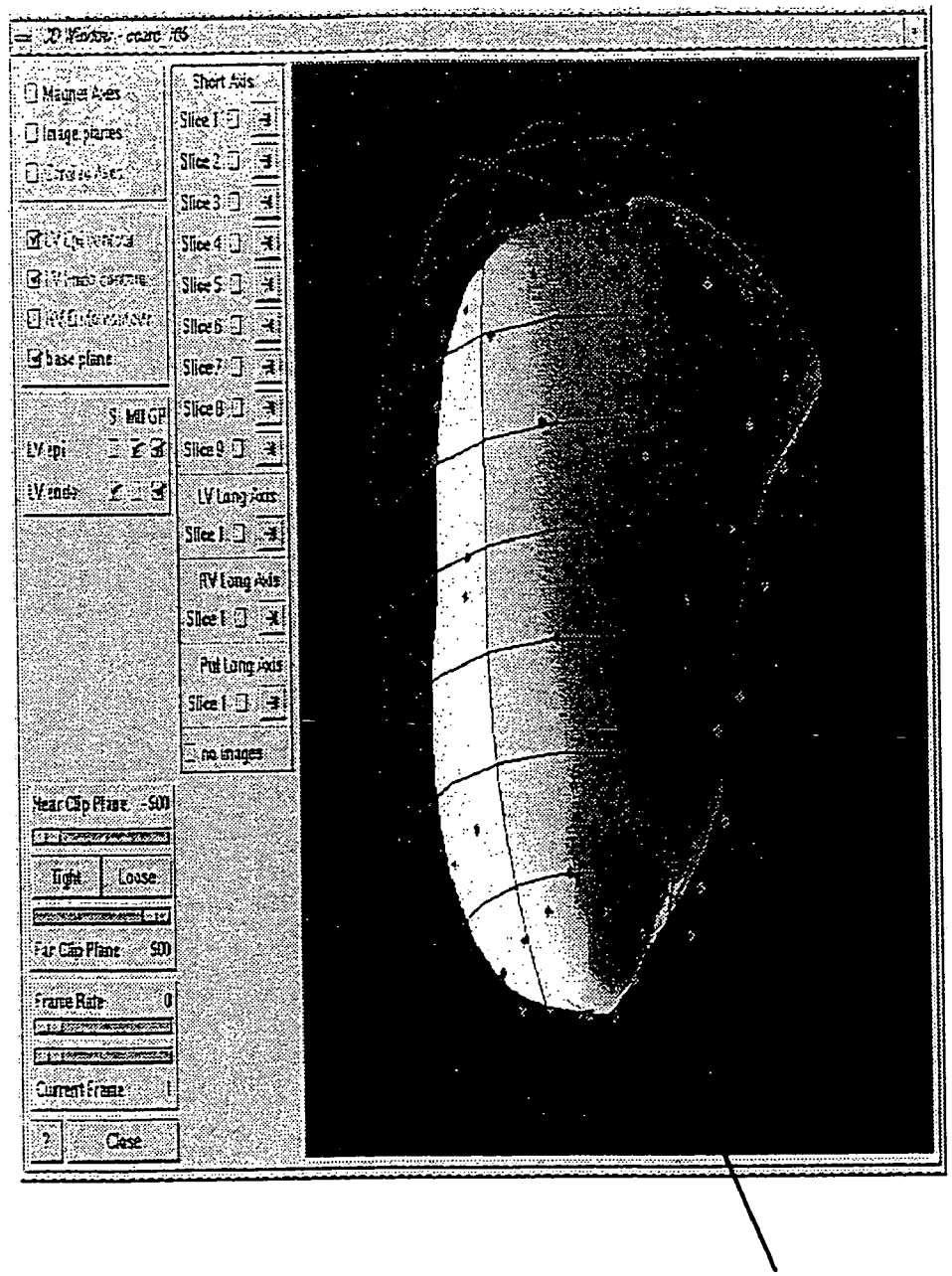

Referring to FIG. 12, the user has elected not to display image planes. The image displayed in panel 56 is instead the estimate endocardial surface rather than individual image planes.

Each boundary or contour is then assessed by the user for appropriateness. If the boundary or contour is unacceptable, the user may define further boundary guide points until such time as the boundary or contour is acceptable, as indicated in FIG. 1 at 124.

Left ventricular cardiac volume, for example, may then be estimated by calculating the volume bounded by the estimate model in the step indicated at 130 in FIG. 1. Left ventricular wall thickness may also be calculated from the estimate model. Left ventricular mass may be calculated from the difference between the volumes enclosed by the endocardial and epicardial contours multiplied by an appropriate constant, for example 1.05 g/ml.

It will be appreciated that the volume, wall thickness and mass of the right ventricle may also be calculated in the same way. Where more than one frame is stored in the memory, the method may be used to measure abnormalities in the left or right ventricle identified through changes in wall thickness over time. The system may also be arranged to calculate area, curvature, angles and other parameters from the estimate model.

Figure 13:
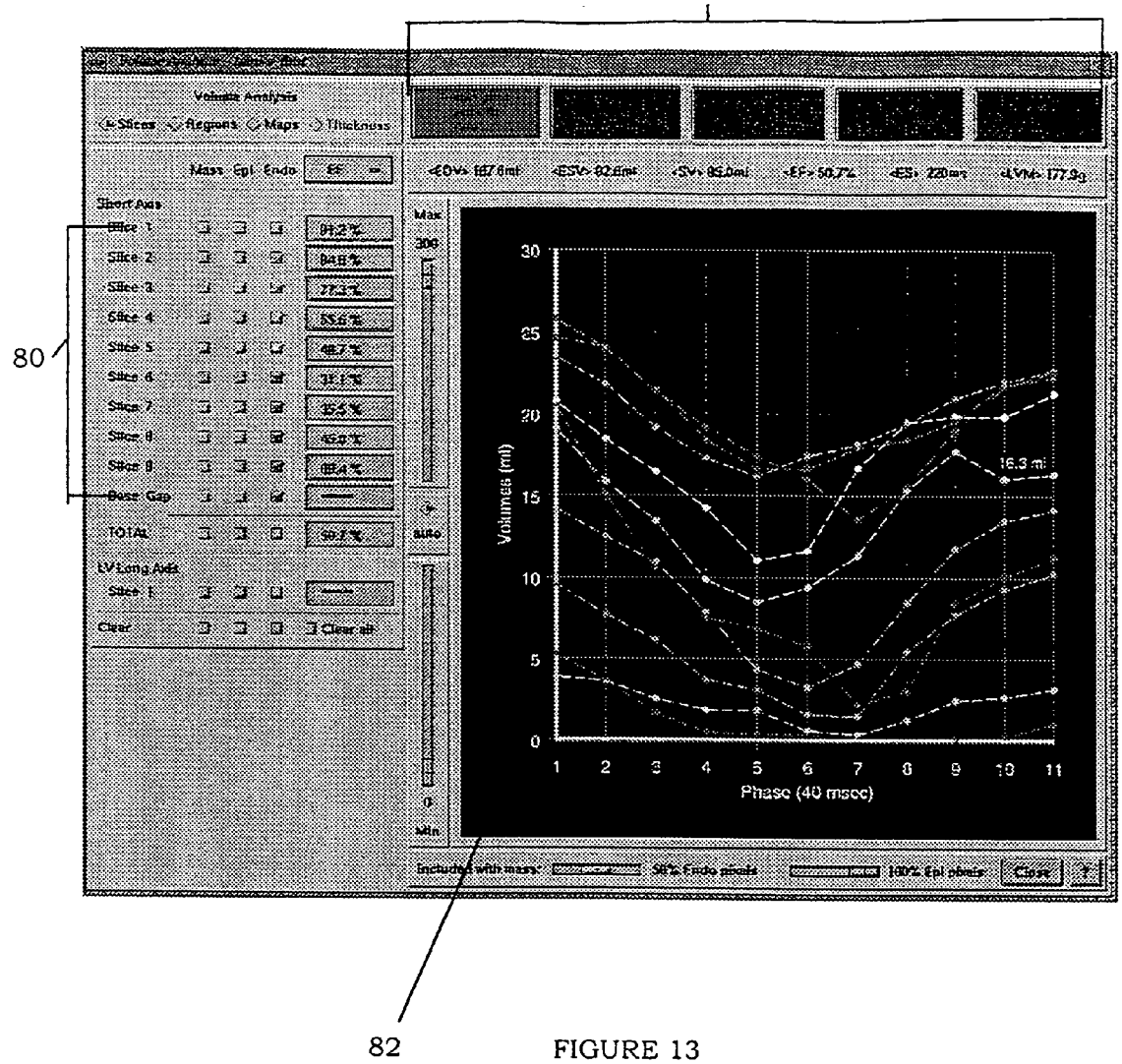
FIGS. 13 to 15 show preferred displays of data obtained from the method and system of the invention.

The method and system of the invention may further provide the results of measurement and analysis in an intuitive, useful and interactive way that the cardiologist can understand and use in patient management. Referring to FIG. 13, the system may display to a user the volumes of blood or muscle associated with each imaging slice. These volumes are preferably determined by calculating the area of the endocardium or epicardium from the estimate model for each slice and multiplying each area by the slice thickness.

Individual slice identifiers are indicated at 80 in a display panel. By clicking in the appropriate box adjacent a slice identifier the user may view a graph indicated at 82 of volume vs time for the mass, endocardium or epicardium respectively. Individual boxes indicated at 84 may display numerical values for end-diastolic and end-systolic volumes, mass, stroke volume and ejection fraction for each slice.

Figure 14:
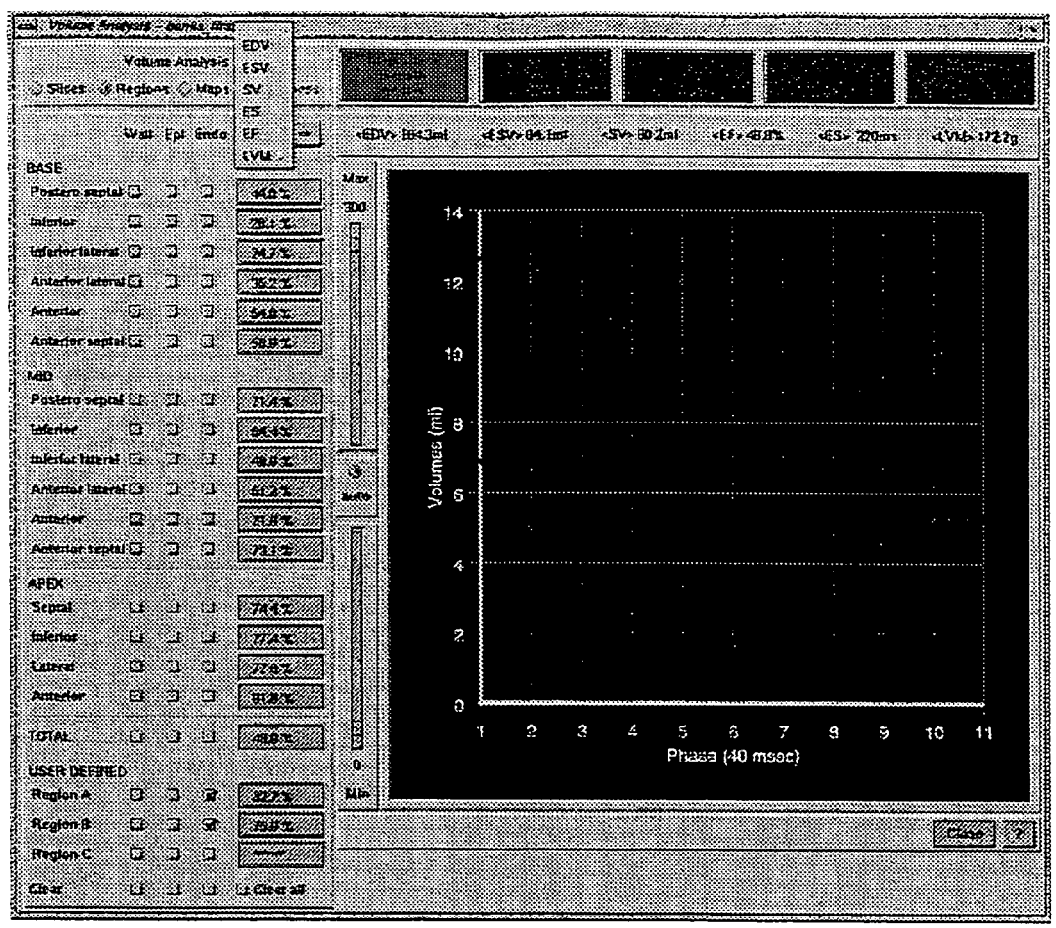

FIG. 14 illustrates display of data similar to the data of FIG. 13. In FIG. 14 regions or sections of the ventricle are displayed according to the standard definitions of the American Society of Echocardiographers. The data displayed in FIG. 14 is useful to a cardiologist as the data is independent of the original scan planes. The data has been acquired by mathematically sampling the model in each of the regions.

Figure 15:
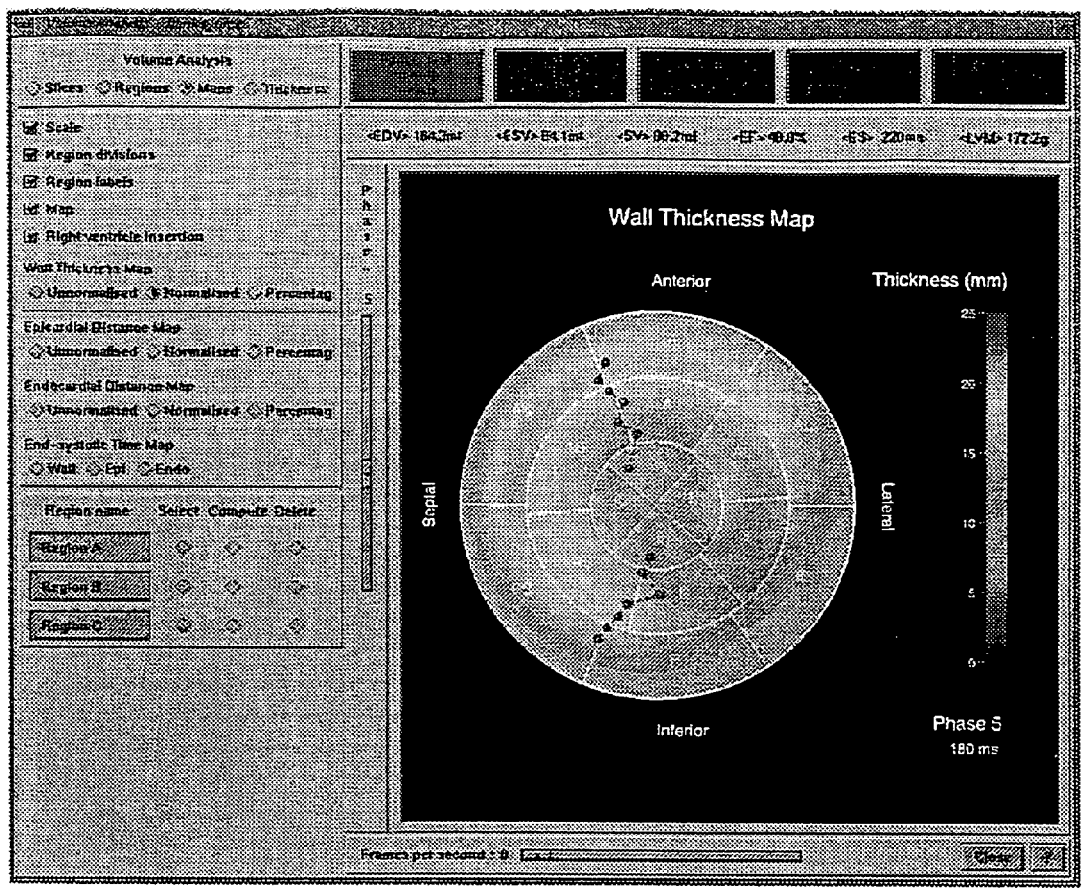

FIG. 15 illustrates a further display in which the left ventricle has been folded out onto a flat surface and the wall thickness at every point mapped in a different colour or shade. This display cines through the cardiac cycle as wall thickness changes. Arbitrary user defined regions can be drawn onto the map and the results shown as a graph, for example regions A, B and C in FIG. 14. The right ventricle insertion with the left ventricle is shown by the dots in the image of the left ventricle. Further buttons on the display switch different parts of the display on and off.

The method may also be used to measure characteristics of other organs for example the lung, the kidney or may be used to measure the wall of a blood vessel. In the case of a kidney the method may be used to measure cortical thickness.

In a further form the invention could be implemented on or associated with scanning apparatus. As the scanner produces images, an operator could insert guide points and update the estimate model. Areas of insufficient data could be identified automatically and the scanner directed to scan these planes automatically.

The method and system of the invention are particularly suited to measuring characteristics of human subjects. It will be appreciated that the same method and system could be used to measure characteristics of organs of other mammals for example rodents, canines and primates. The same technique could also be applied to the task of measuring the size and/or geometry of a cell.

The foregoing describes the invention including preferred forms thereof. Alterations and modifications as will be obvious to those skilled in the art are intended to be incorporated within the scope hereof as defined by the accompanying claims.

The invention claimed is:

1. A method of assessing one or more characteristic(s) of an organ or part thereof from multiple images acquired of the organ or part thereof, the method including forming a fit between a reference model of the geometric shape of the organ or part thereof and a series of acquired images of the organ or part thereof by a series of user interactive steps which consist essentially of:

defining the spatial position of at least two of the acquired images;

forming an initial fit between the reference model and the acquired images by displaying one or more of the acquired image(s) to a user, manually user defining one or more reference markers on the acquired image(s), and initially fitting the model to the acquired image(s) by reference to the reference markers on the image(s);

displaying to a user an acquired image of the subject organ or part thereof, the image including at least one organ boundary derived from the intersection of a surface of the organ with the plane of the image;

displaying to the user a representation of the initial fit of the reference model by displaying on the acquired image a representation of the intersection of the model with the plane of the image;

manually user-defining one or more reference guide points on a user-selected organ boundary on the image displayed to the user, for which the spatial positions have been defined;

on user definition of the or each reference guide point, converting the guide point(s) to coordinates which define the three dimensional position of the guide point(s); improving the fit of the model to the guide point(s) to form an improved fit of the model for the organ or part; displaying to the user a representation of the improved fit of the model by displaying on an acquired image a representation of the intersection of the improved fit of the model with the plane of the user-selected image;

manually user-defining one or more further reference guide points on at least one further user-selected image displayed to the user, for which the spatial positions have been defined; and on user definition of the or each reference guide point, converting the further guide point(s) to coordinates which define the three dimensional position of the guide point(s); and further improving the fit of the model by fitting the model to said further reference guide point(s), to thereby form a further improved fit of the estimate model for the organ or part which enables assessing the one or more characteristic(s) from the estimate model.

2. A method as claimed in claim 1 wherein the step of forming the initial fit between the reference model and the images, includes the steps of defining a point associated with the reference marker(s), on each of two images defining a reference line in 3-dimensional space between the points, calculating the distance as a function of the length of the reference line, and at least approximately matching the scale of the reference model and the images according to the distance between the points.

3. A method as claimed in claim 2 wherein the reference model comprises a mathematically defined reference model.

4. A method as claimed in claim 3 wherein the reference model comprises an ellipsoid having a reference line as a central axis and one or more surface points, each surface point specified by a radial distance from the central axis.

5. A method as claimed in claim 1 further comprising the step of performing image processing on one or more of the images.

6. A method as claimed in claim 1 further comprising the step of calculating the volume of the subject organ or part from the estimate model.

7. A method as claimed in claim 1 further comprising the step of calculating the mass of the subject organ or part from the estimate model.

8. A method as claimed in claim 1 wherein the subject organ comprises a ventricle of the heart and the characteristics measured include ventricular mass, endocardial volume and/or wall thickness of all of the ventricle or part thereof.

9. A method as claimed in claim 1 wherein the subject organ comprises a ventricle of the heart and the characteristics measured include ventricular abnormalities identified through changes in wall thickness over time.

10. A method as claimed in claim 1 wherein the subject organ comprises a kidney and the characteristics measured include cortical thickness.

11. A system for assessing one or more characteristic(s) of an organ or part thereof from multiple images acquired of the organ or part thereof by forming a fit between a reference model of the geometric shape of the organ or part thereof and a series of acquired images of the organ or part thereof by a series of user interactive steps, the system comprising:

a memory in which is stored the spatial position of at least two of the images;

initial fitting means configured to form an initial fit between the reference model and the acquired images by displaying one or more reference markers to a user, manually user defining one or more reference markers on the acquired image(s), and initially fitting the model to the acquired image(s) by reference to the reference markers on the image(s);

a display configured to display to a user an acquired image of the subject organ or part thereof, the image including at least one organ boundary derived from the intersection of a surface of the organ with the plane of the user-selected image, the display further configured to display to the user a representation of the initial fit of the reference model by displaying on the image a representation of the intersection of the model with the plane of the image;

reference guide point definition means enabling a user to manually define one or more reference guide points on a user-selected organ boundary on the image displayed to the user, for which the spatial positions have been defined;

conversion means configured, on user definition of the or each reference guide point, to convert the guide point(s) to coordinates which define the three dimensional position of the guide point(s);

fit improving means configured, on user definition of the or each reference guide point, to improve the fit of the model to the guide point(s) to form an improved fit of the model for the organ or part thereof;

the display further configured, on user definition of the or each reference guide point, to display to the user a representation of the improved fit of the model by displaying on an acquired image a representation of the intersection of the improved fit of the model with the plane of the image;

the reference guide point definition means further configured to enable a user to manually define one or more further reference guide points on at least one further image displayed to the user, for which the spatial positions have been defined;

the conversion means further configured, on user definition of the or each reference guide point, to convert the additional guide point(s) to coordinates which define the three dimensional position of the guide points; and the fit improving means further configured, on user definition of the or each reference guide point, to further improve the fit of the model by fitting the model to said further reference guide point(s), to thereby form a further improved fit of the estimate model for the organ or part which enables assessing the one or more characteristic(s) from the estimate model.

12. A system as claimed in claim 11 wherein the initial fitting means is configured to form the initial fit between the reference model and the images by defining a reference line in three-dimensional space between the points, calculating the distance as a function of the length of the reference line, and at least approximately matching the scale of the reference model and the images according to the distance between the points.

13. A system as claimed in claim 12 wherein the reference model comprises a finite element model.

14. A system as claimed in claim 13 wherein the reference model comprises an ellipsoid having the reference line as a central axis and one or more surface points, each surface point specified by a radial distance from the central axis.

15. A system as claimed in claim 11 further comprising image processing means configured to perform image processing on one or more of the images.

16. A system as claimed in claim 11 further comprising volume calculation means configured to calculate the volume of the subject organ or part from the estimate model.

17. A system as claimed in claim 11 further comprising mass calculation means configured to calculate the mass of the subject organ or part from the estimate model.

18. A system as claimed in claim 11 wherein the subject organ comprises a ventricle of the heart and the characteristics measured include ventricular mass, endocardial volume and/or wall thickness of all of the ventricle or part thereof.

19. A system as claimed in claim 11 wherein the subject organ comprises a ventricle of the heart and the characteristics measured include ventricular abnormalities identified through changes in wall thickness over time.

20. A system as claimed in claim 11 wherein the subject organ comprises a kidney and the characteristics measured include cortical thickness.

21. A computer readable medium having stored thereon a computer program for assessing one or more characteristic(s) of an organ or part thereof of a subject from multiple images acquired of the organ or part thereof by forming a fit between a reference model of the geometric shape of the organ or part thereof and a series of acquired images of the organ or part thereof by a series of user interactive steps, the program comprising:

storage means configured to store the spatial position of at least two of the images;

initial fitting means configured to form an initial fit between the reference model and the acquired images by displaying at least two of the acquired images to a user, manually user defining one or more reference markers on the acquired image(s), and initially fitting the model to the acquired image(s) by reference to the reference markers on the image(s);

a display configured to display to a user an acquired image of the subject organ or part thereof, the image including at least one organ boundary derived from the intersection of a surface of the organ with the plane of the user-selected image, the display further configured to display to the user a representation of the initial fit of the reference model by displaying on the acquired image a representation of the intersection of the model with the plane of the image;

reference guide point definition means enabling a user to manually define one or more reference guide points on a user-selected organ boundary on the image displayed to the user, for which the spatial positions have been defined;

conversion means configured, on user definition of the or each reference guide point, to convert the guide point(s) to coordinates which define the three-dimensional position of the guide point(s);

fit improving means configured, on user definition of the or each reference guide point, to improve the fit of the model to the guide point(s) to form an improved fit of the model for the organ or part thereof;

the display further configured, on user definition of the or each reference guide point, to display to the user a representation of the improved fit of the model by displaying on an acquired image a representation of the intersection of the improved fit of the model with the plane of the user-selected image;

the reference guide point definition means further configured to enable a user to manually define one or more further reference guide points on at least one further acquired image displayed to the user, for which the spatial positions have been defined;

the conversion means further configured, on user definition of the or each reference guide point, to convert the additional guide point(s) to coordinates which define three-dimensional position of the guide points; and the fit improving means further configured, on user definition of the or each reference guide point, to further improve the fit of the model by fitting the model to said further reference guide point(s), to thereby form a further improved fit of the estimate model for the organ or part which enables assessing the one or more characteristic(s) from the estimate model.

22. A computer readable medium as claimed in claim 21 wherein the initial-fitting means is configured to form the initial fit between the reference model and the images by defining a point associated with the reference marker(s) on each of two images, defining a reference line in three-dimensional space between the points, calculating the distance as a function of the length of the reference line, and at least approximately matching the scale of the reference model and the images according to the distance between the points.

23. A computer readable medium as claimed in claim 22 wherein the reference model comprises a finite element model.

24. A computer readable medium as claimed in claim 23 wherein the reference model comprises an ellipsoid having the reference line as a central axis and one or more surface points, each surface point specified by a radial distance from the central axis.

25. A computer readable medium as claimed in claim 21 further comprising image processing means configured to perform image processing on one or more of the images.

26. A computer readable medium as claimed in claim 21 further comprising volume calculation means configured to calculate the volume of the subject organ or part from the estimate model.

27. A computer readable medium as claimed in claim 21 further comprising mass calculation means configured to calculate the mass of the subject organ or part from the estimate model.

28. A computer readable medium as claimed in claim 21 wherein the subject organ comprises a ventricle of the heart and the characteristics measured include ventricular mass, endocardial volume and/or wall thickness of all of the ventricle or part thereof.

29. A computer readable medium as claimed in claim 21 wherein the subject organ comprises a ventricle of the heart and the characteristics measured include ventricular abnormalities identified through changes in wall thickness over time.

30. A computer readable medium as claimed in claim 21 wherein the subject organ comprises a kidney and the characteristics measured include cortical thickness.

* * * * *